US008590383B2

(12) United States Patent
Brignac et al.

(10) Patent No.: US 8,590,383 B2
(45) Date of Patent: Nov. 26, 2013

(54) ULTRASONIC INSPECTION PROBE CARRIER SYSTEM FOR PERFORMING NON-DESTRUCTIVE TESTING

(75) Inventors: Jacques L. Brignac, Simsbury, CT (US); Robert E. Lucas, Southbury, CT (US)

(73) Assignee: ALSTOM Technology Ltd, Baden (CH)

( * ) Notice: Subject to any disclaimer, the term of this patent is extended or adjusted under 35 U.S.C. 154(b) by 1260 days.

(21) Appl. No.: 12/144,756

(22) Filed: Jun. 24, 2008

(65) Prior Publication Data
US 2009/0314089 A1 Dec. 24, 2009

(51) Int. Cl.
*G01N 9/24* (2006.01)
(52) U.S. Cl.
USPC .................. 73/640; 73/622; 73/635; 376/252
(58) Field of Classification Search
USPC ........... 73/622, 640, 618, 621, 633, 634, 635; 376/249, 252
See application file for complete search history.

(56) References Cited

U.S. PATENT DOCUMENTS

| | | | |
|---|---|---|---|
| 2,742,259 A | | 4/1956 | Boucher |
| 2,908,161 A | * | 10/1959 | Bincer ............................ 73/622 |
| 3,602,036 A | * | 8/1971 | Peterson ......................... 73/633 |
| 3,809,607 A | * | 5/1974 | Burns et al. .................... 376/249 |
| 3,998,286 A | * | 12/1976 | Ponikelsky et al. .......... 180/9.48 |
| 4,006,359 A | | 2/1977 | Sullins et al. |
| 4,108,004 A | | 8/1978 | Murakami |
| 4,270,389 A | * | 6/1981 | Shiraiwa et al. ................ 73/612 |
| 4,279,158 A | | 7/1981 | Kajiyama et al. |
| 4,304,133 A | * | 12/1981 | Feamster, III .................... 73/633 |
| 4,330,865 A | * | 5/1982 | Hyde et al. ..................... 376/249 |
| 5,105,658 A | * | 4/1992 | Jaafar et al. ................... 73/865.8 |
| 5,128,094 A | * | 7/1992 | Muller et al. .................. 376/249 |
| 5,289,436 A | * | 2/1994 | Terhune ......................... 367/191 |

(Continued)

FOREIGN PATENT DOCUMENTS

| | | |
|---|---|---|
| DE | 19529782 | 2/1997 |
| EP | 0378480 | 10/1990 |
| GB | 2015736 | 9/1979 |
| GB | 1559469 | 1/1980 |

OTHER PUBLICATIONS

Harfang Microtechniques Inc. [online]; [retrieved on Sep. 2006]; retrieved from the internet http://www.harfangmicro.com, Boiler Tube Imaging, 2p, Quebec, Que-Canada.

(Continued)

*Primary Examiner* — Daniel S Larkin
*Assistant Examiner* — Samir M Shah

(57) ABSTRACT

An ultrasonic probe carrier includes a base, a first side arm having a first end thereof attached to the base and a second end thereof extending outwardly from the base on one side of a tube, and a second side arm having a first end thereof attached to the base and a second end thereof extending outwardly from the base on an opposite side of the tube, at least a portion of the first and second side arms being biased towards each other to removably secure the carrier around at least a portion of a circumference of the tube. An ultrasonic probe is attached to the base, and the carrier and ultrasonic probe are rotatable around the tube to scan at least one of: the circumference of the tube and a weld disposed around the circumference of the tube.

29 Claims, 3 Drawing Sheets

(56) References Cited

U.S. PATENT DOCUMENTS

| | | | |
|---|---|---|---|
| 5,359,898 A | 11/1994 | Latimer | |
| 5,454,267 A | 10/1995 | Moreau | |
| 5,473,953 A * | 12/1995 | Appel | 73/866.5 |
| 5,476,010 A | 12/1995 | Fleming et al. | |
| 5,535,628 A * | 7/1996 | Rutherford | 73/622 |
| 5,549,004 A * | 8/1996 | Nugent | 73/622 |
| 5,635,780 A * | 6/1997 | Kohlert et al. | 310/68 R |
| 5,650,579 A * | 7/1997 | Hatley et al. | 73/865.8 |
| 5,784,425 A * | 7/1998 | Morlan | 376/249 |
| 5,857,534 A * | 1/1999 | DeVault et al. | 180/21 |
| 6,100,711 A * | 8/2000 | Hatley | 324/765.01 |
| 6,230,568 B1* | 5/2001 | Winston et al. | 73/601 |
| 6,271,670 B1 | 8/2001 | Caffey | |
| 6,282,964 B1 | 9/2001 | Hancock | |
| 6,373,914 B1 | 4/2002 | Gill et al. | |
| 6,497,159 B1* | 12/2002 | Lavoie | 73/866.5 |
| 6,502,452 B1 | 1/2003 | Gill et al. | |
| 6,567,795 B2 | 5/2003 | Alouani | |
| 6,672,413 B2* | 1/2004 | Moore et al. | 180/9.21 |
| 6,748,808 B2 | 6/2004 | Lam et al. | |
| 6,799,466 B2 | 10/2004 | Chinn | |
| 6,889,783 B1* | 5/2005 | Moore et al. | 180/9.21 |
| 6,904,817 B2* | 6/2005 | Davis et al. | 73/865.8 |
| 6,920,792 B2 | 7/2005 | Flora | |
| 7,077,020 B2* | 7/2006 | Langley et al. | 73/865.8 |
| 7,201,055 B1* | 4/2007 | Bagley et al. | 73/618 |
| 7,555,966 B2* | 7/2009 | Bagley et al. | 73/865.8 |
| 7,587,942 B2* | 9/2009 | Smith et al. | 73/622 |
| 7,681,452 B2* | 3/2010 | Bagley et al. | 73/623 |
| 7,987,723 B2* | 8/2011 | Maruyama et al. | 73/633 |
| 8,365,601 B2* | 2/2013 | Minachi et al. | 73/602 |
| 2003/0033880 A1* | 2/2003 | Lam et al. | 73/627 |
| 2003/0188589 A1 | 10/2003 | Harthorn et al. | |
| 2004/0083815 A1* | 5/2004 | Lam et al. | 73/618 |
| 2004/0255678 A1* | 12/2004 | Nagashima et al. | 73/620 |
| 2005/0217394 A1* | 10/2005 | Langley et al. | 73/865.8 |
| 2008/0087112 A1* | 4/2008 | Bagley et al. | 73/865.8 |
| 2008/0087113 A1* | 4/2008 | Bagley et al. | 73/865.8 |

OTHER PUBLICATIONS

Russell NDE Systems Inc., [online]; [retrieved 2007]; retrieved from the internet http://www.russelltech.com/ut/DarisMain.html, 2007, An Innovation in Tube Inspection Daris,1p, Edmonton, Alberta, Canada.

Wikipedia. [online]; [retrieved on Apr. 13, 2007]; retrieved from the Internet http://en.wikipedia.org/wiki/Internal_Rotary_Inspection_System, Internal rotary inspection system 1p.

NDT, [online]; [retrieved on Apr. 13, 2007]; retrieved from the Internet http://www.ndt.net/apcndt2001/papers/7/7/htm Charles Panos, Condition Monitoring-Process Plant Tube Inspection and Ongoing Commitment by Plant Owners and Operators, 10p, International Tube Testing Pty Ltd, Qld, Australia.

U.S. Appl. No. 11/751,057, filed May 21, 2007, Title: Boiler Tube Inspection Probe with Centering Mechanism and Method of Operating the Same.

U.S. Appl. No. 11/829,208 filed Jul. 27, 2007, Title: Portable Scanner Device for Metallurgical, Nondestructive Testing.

European Search Report (EP09159911.8) dated Mar. 15, 2011.

European Search Report (for EP09159911.8) dated Jan. 28, 2013.

\* cited by examiner

ULTRASONIC INSPECTION PROBE CARRIER SYSTEM FOR PERFORMING NON-DESTRUCTIVE TESTING

TECHNICAL FIELD

The present disclosure relates generally to a carrier system for an ultrasonic probe used in performing nondestructive testing of tubes and welds of tubes.

BACKGROUND

Testing of pressure parts and various diameter tubes or piping using nondestructive testing techniques is an arduous task, particularly when testing seam welds. For example, a boiler system having multiple tubes linearly arranged in a fixed position (e.g., waterwall tubes) and with a fixed, limited amount of space between the tubes may be difficult to inspect with precision. Typically, using ultrasonic techniques (UT), an operator manually scans the desired area of the tube with a hand-held UT probe that delivers signals (sound waves) through the tubing and receives feedback measurements as a result of the scanning. Clearly such a manual process is susceptible to inaccuracies, since a human operator's fine motor skills while traversing the tube, either longitudinally along the length or circumferentially, may not be entirely stable or consistent, which translates to less than optimal readings (e.g., missed cracks or wall degradation, false positives, and other such errors).

What is needed, therefore, is a way to provide ultrasonic testing of tube-to-tube welds or tube to header welds for multiple linearly arranged and fixed tubing having limited space between the tubing.

SUMMARY

According to the aspects illustrated herein, there is provided an ultrasonic probe carrier includes a base, a first side arm having a first end thereof attached to the base and a second end thereof extending outwardly from the base on one side of a tube, and a second side arm having a first end thereof attached to the base and a second end thereof extending outwardly from the base on an opposite side of the tube, at least a portion of the first and second side arms being biased towards each other to removably secure the carrier around at least a portion of a circumference of the tube. An ultrasonic probe is attached to the base, and the carrier and ultrasonic probe are rotatable around the tube to scan at least one of: the circumference of the tube and a weld disposed around the circumference of the tube. The above described and other features are exemplified by the following figures and detailed description.

BRIEF DESCRIPTION OF THE DRAWINGS

Referring now to the figures, which are exemplary embodiments, and wherein the like elements are numbered alike.

DETAILED DESCRIPTION

An ultrasonic inspection system ("system") for providing nondestructive testing of tubing and tube welds having restricted or limited space therebetween is provided. The system includes an ultrasonic probe carrier having a low profile that enables the system to access tubes and welds having limited or restricted space among them. The carrier also increases the effectiveness of nondestructive testing techniques due to its compact and unique design. As used herein, the term "tube" can include any cylindrical body.

Figure 1:
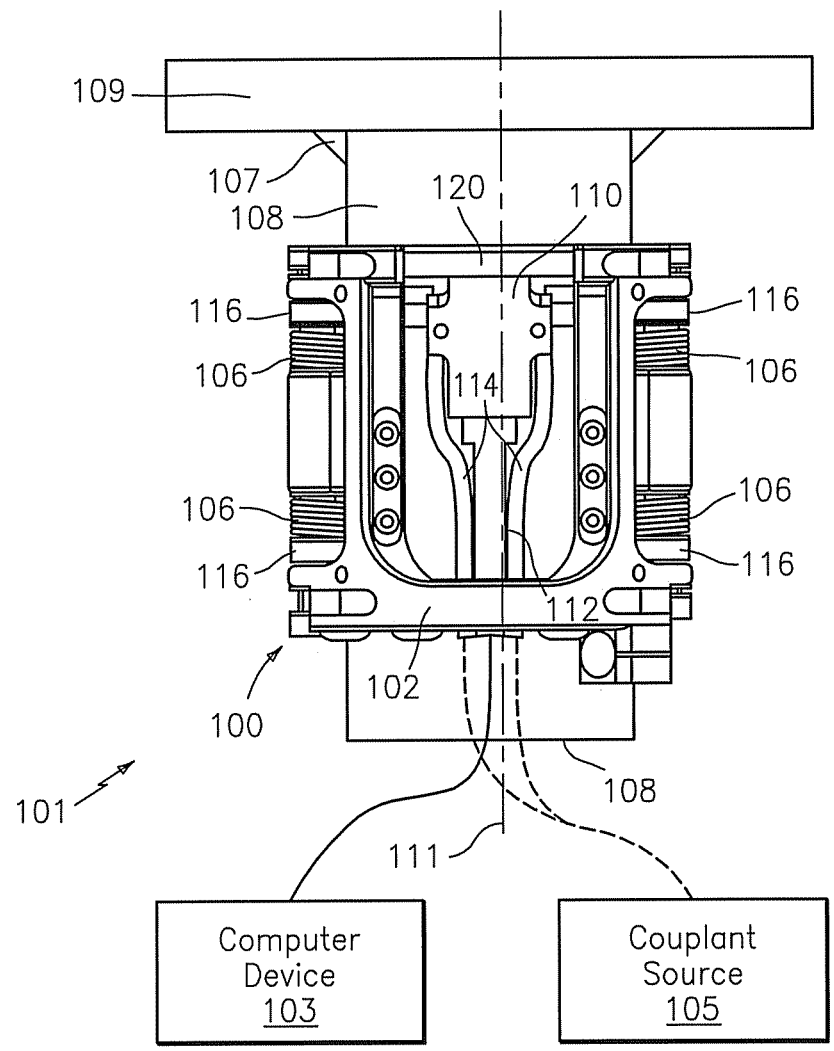
FIG. 1 is planar side view of an exemplary ultrasonic inspection system.
Figure 2:
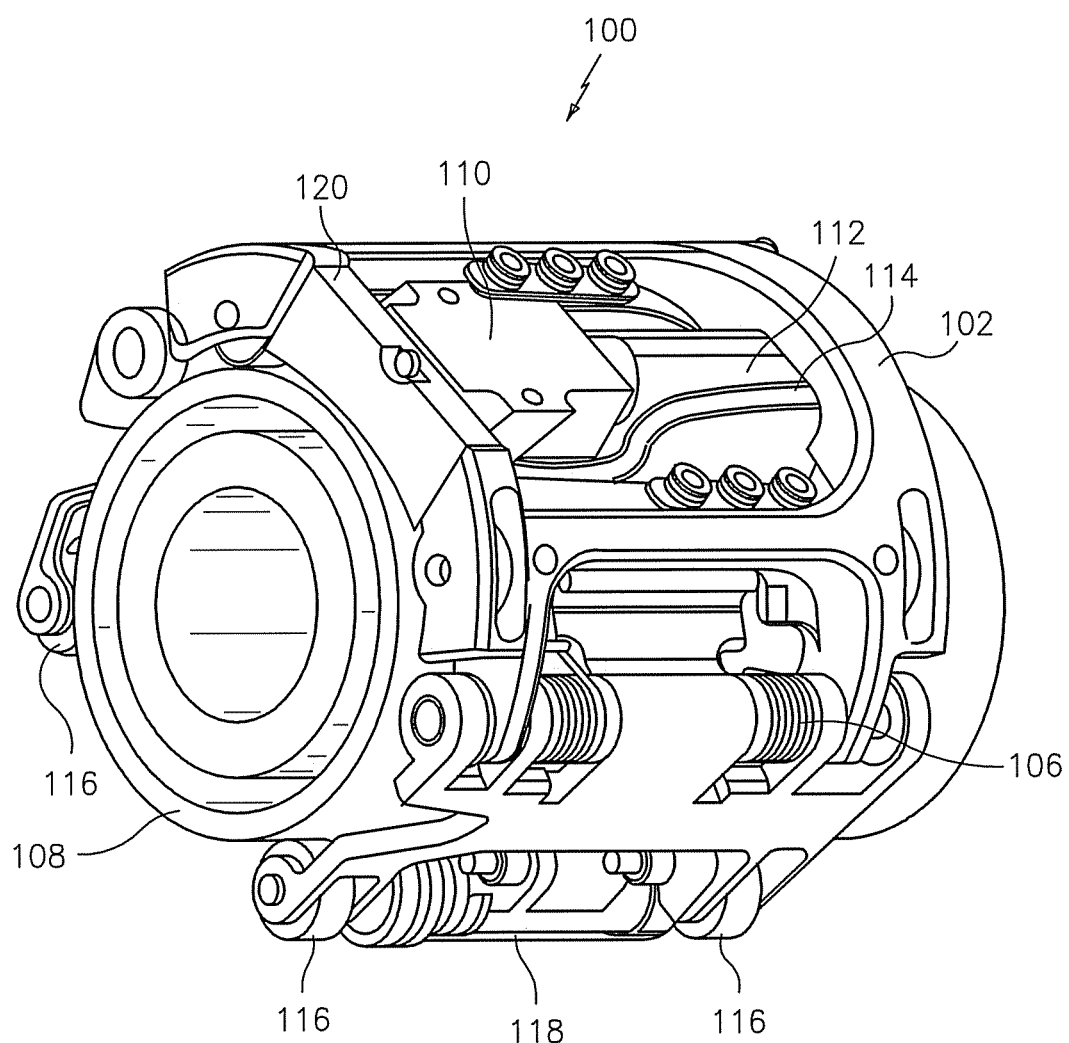
FIG. 2 is perspective view of a probe carrier for the exemplary ultrasonic inspection probe carrier system of FIG. 1.
Figure 3:
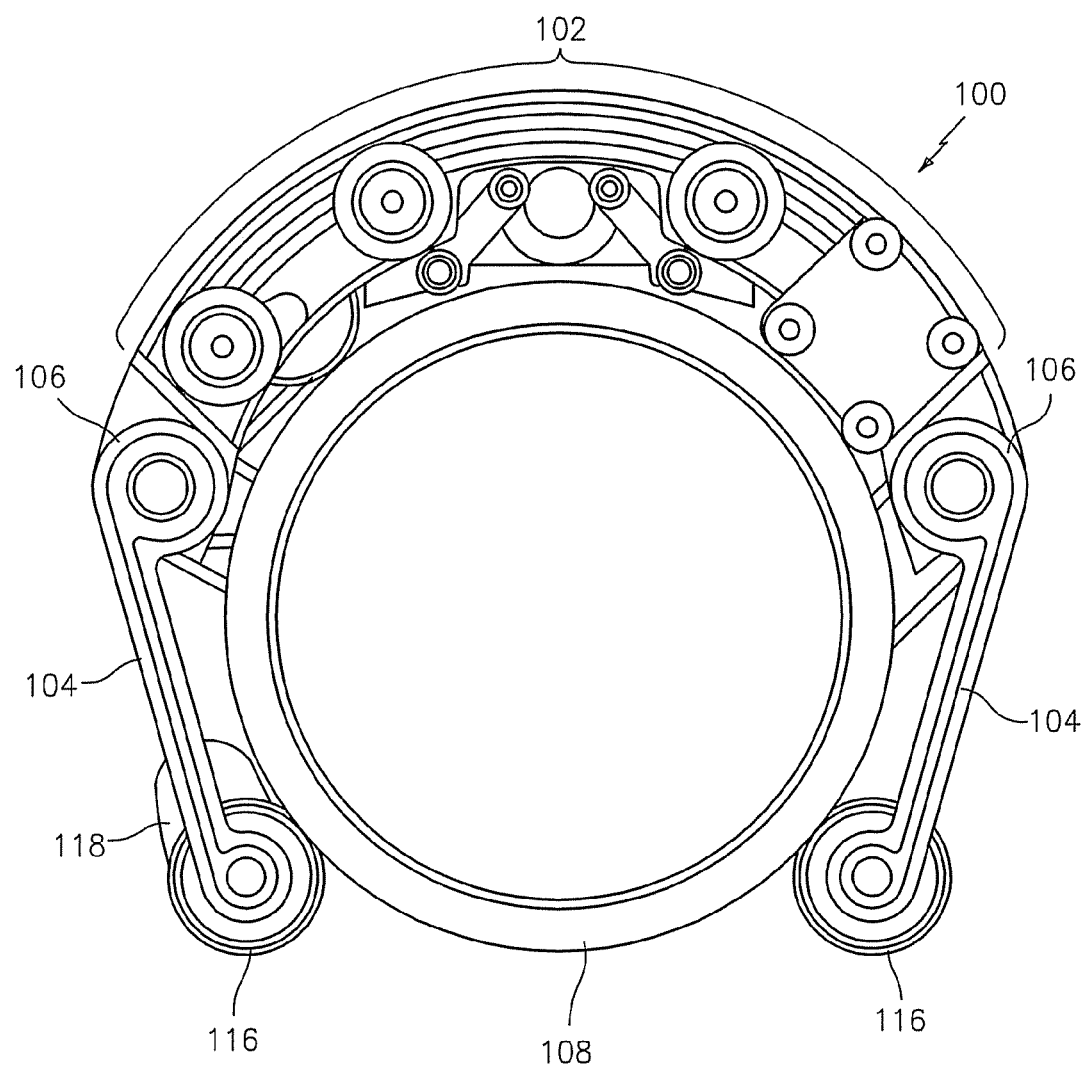
FIG. 3 is a planar bottom view of the probe carrier for the exemplary ultrasonic inspection probe carrier system of FIGS. 1 and 2.

Turning now to FIGS. 1-3, the system 101 for performing nondestructive testing will now be described in accordance with exemplary embodiments. The system 101 includes a portable, self-contained probe carrier 100, an ultrasonic inspection probe 110, a computer device 103, and a couplant source 105. The carrier 100 includes a base 102 having an arc shape along a longitudinal axis thereof and also has a thin depth, such that it can circumnavigate tubes 108 and tube welds having limited or restrictive space therebetween. The longitudinal axis of the base 102 extends parallel to a longitudinal axis 111 of a tube 108 to be inspected or a tube 108 having a weld to be inspected, and the arc of the base 102 may be open at an angle sufficient to accommodate tubes 108 or welds of different diameters.

The carrier 100 further includes a first side arm 104 having a first end thereof attached to a side of the base 102 and a second, distal end thereof extending outwardly from the base 102. Carrier 100 also includes a second side arm 104 having a first end thereof attached to an opposing side of the base 102 and a second, distal end thereof extending outwardly from the base 102. The side arms 104 extend on opposite sides of the tube 108. At least a portion of the side arms 104 are biased towards each other to engage the tube 108 such that carrier 100 is removably disposed around at least a portion of a circumference of the tube 108. In the embodiment shown, the first end of each side arm 104 is hingeably secured to the base 102, with torsion springs 106 arranged at the hinges to bias the side arms 104 toward each other. The biasing force provided by springs 106 secure the carrier 100 to the tube 108 and allow the side arms 104 to adapt to tubes 108 of different diameters.

Disposed on each of the first and second ends of each of the side arms 104 are wheels 116. The wheels 116 have a rotational axis that extends generally parallel to the longitudinal axis 111, which enables the carrier 100 rotate around the tube 108 to circumferentially scan the tube 108 or weld on tube 108. In one embodiment, the wheels 116 may be magnetic for providing greater security in fixing the carrier 100 to the tube 108. Where magnetic wheels 116 are used, it is contemplated that the magnets may provide sufficient biasing force to secure the carrier 100 to the tube 108 without springs 106. It is also contemplated that the side arms 104 may be rigid with respect to the base 102 (not hingeably secured to the base), with wheels 116 being the only portion of side arms 104 that are biased towards each other (e.g., by spring or magnetic force) to secure the carrier 100 to the tube 108.

The ultrasonic probe 110 is attached to an upper portion of the base 102 of carrier 100. The ultrasonic probe 110 operates in a known manner by transmitting ultrasonic sound energy into a region of the tube 108 to be tested (e.g., the tube material itself or a weld on the tube), receiving a portion of the energy reflected back by discontinuities in the wave path (such as an crack or imperfection in the tube 108), and transforming the reflected energy into an electrical signal. The probe 110 includes a waveguide (wedge) 120, which is contoured to the radius of the tube 108. Waveguide 120 may be arranged to scan: in a direction generally perpendicular to the longitudinal axis 111, in a direction generally parallel to longitudinal axis 111, or in both perpendicular and parallel directions. The waveguide is detachable, and may be interchanged with waveguides having different scan directions and contour radii. While only a portion of waveguide 120 is shown, it is contemplated that waveguide 120 may extend beneath probe 110.

The probe 110 includes a cable 112 extending from a lower edge of the probe 110 in a longitudinal direction of the base 102 and exiting out a hole formed at a lower portion of the base 102. The cable 112 is operable for transmitting electrical signals between the probe 110 and a computer device 103 (e.g., a general purpose computer) having memory to record the electrical signals received from the probe 110 and display screen to allow an operator to view a visual indication of the electrical signals received from the probe 110. Using various applications, the data acquired and recorded from the inspection may be converted in graphical form and displayed by computer device 103. The graphical form of the data may illustrate qualitative and quantitative results of the inspections via the ultrasonic probe 110. For example, the results may include defects in the weld under inspection, as well as the extent of the defects (such as size, range, and depth).

The carrier 100 also includes a first and second couplant tubes 114 extending in a longitudinal direction on opposing sides of the probe 110. The couplant tubes 114 are in fluid communication with a couplant source 105, such as a pressurized container or pump, and carrying a couplant material from the source 105 to the tube 108 or weld under inspection at the location of the probe 110. The couplant material may be water, gel, or other suitable material to facilitate the transmission of ultrasonic waves between the probe 110 and tube 108.

The carrier 100 further includes an encoder 118 disposed on one of the side arms 104 at the second end thereof. The encoder 118 is operable for providing a reference point for a physical location at which the inspection is initiated, as well as a means for tracking and recording the responses from the probe 110 with respect to the ongoing inspection. The encoder 118 is small in size enabling the depth of the side arm 104, to which it is attached, to be thin. For example, the encoder 118 may include a wheel (e.g., wheel 116) that rests on the tube 108 and rotates as the carrier 100 is moved relative to the tube 108. A sensor within the encoder detects movement of the wheel, which indicates the relative position of the probe 110 as it moves along the tube 108. The encoder provides electrical signals indicative of this position to the computer device via cable 112, thus allowing the computer device to correlate probe 110 readings with specific locations on tube 108. While encoder 118 is preferably attached to a side arm 104, it is contemplated that encoder may instead be attached to the base 102.

In an exemplary embodiment, the base 102 and the side arms 104 of the carrier 100 are configured to have a depth that is substantially equal to the thickness of the encoder 118 and probe 110, such that the carrier 100, allows the probe 110 to perform low profile scanning and freely encircles the outer portions of the tube 108 under inspection without interference from adjacent tube 108s.

As previously noted, wave guide 120 may be arranged to direct ultrasonic waves from probe 110 in a direction generally parallel to the longitudinal axis 111 of tube 108, thus allowing probe 110 to scan a weld 107 joining tube 108 to a surface 109 extending in a plane generally perpendicular to tube 108. For example, with wave guide 120, probe 110 can scan welds between tube 108 and flanges, headers, plates and the like. Advantageously, the wave guide 120 may be disposed at the upper edge of the carrier 100, such that upon performing the inspection, there is little or no space between the wave guide 120 and the weld 107 being tested. The carrier 100 can then be rotated around the tube 108 to scan the weld around the entire circumference of the tube 108.

The carrier 100 may be manually rotated around the circumference of the tube 108. Alternatively, the carrier 100 may include a motor (not shown) that automatically rotates the carrier 100 around the circumference of the tube 108 or weld under testing.

As described above, system 101 provides nondestructive testing of tubing and tube welds having restricted or limited space therebetween. The carrier 100 is configured to have a low profile that enables the system to access tubes and welds having limited or restricted space among them. The carrier 100 allows testing of welds between a pipe and a flange, header, plate, or the like, around the entire circumference of the pipe. The carrier 100 also increases the effectiveness of nondestructive testing techniques due to its compact and unique design.

While the invention has been described with reference to various exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A system for performing nondestructive testing on a tube, comprising:
   an ultrasonic probe carrier including:
      a curved base,
      a first side arm having a first end thereof attached to the curved base and a second end thereof extending outwardly from the curved base on one side of the tube, and
      a second side arm having a first end thereof attached to the curved base and a second end thereof extending outwardly from the curved base on an opposite side of the tube, at least a portion of the first and second side arms being biased towards each other to removably secure the ultrasonic probe carrier around at least a portion of a circumference of the tube; and
   an ultrasonic probe attached to the ultrasonic probe carrier, wherein the ultrasonic probe carrier and the ultrasonic probe are rotatable around the tube to scan at least one of the circumference of the tube and a weld disposed around the circumference of the tube.

2. The system of claim 1, further comprising:
   a couplant tube attached to the ultrasonic probe carrier, the couplant tube arranged to direct a couplant material proximate the ultrasonic probe.

3. The system of claim 1, further comprising:
   wheels disposed on each of the first and second side arms, the wheels having axes of rotation disposed generally parallel to a longitudinal axis of the tube to facilitate rotation of the ultrasonic probe carrier around the tube.

4. The system of claim 3, wherein the wheels are magnetic.

5. The system of claim 3, wherein the wheels on the first and second side arms are biased towards each other to removably secure the ultrasonic probe carrier around the portion of the circumference of the tube and the first and second arms have a curved shape.

6. The system of claim 1, wherein the first and second side arms are biased towards each other by a spring force.

7. The system of claim 1, further comprising:
an encoder disposed on the ultrasonic probe carrier, wherein the encoder provides a signal indicative of a location of the ultrasonic probe relative to the tube.

8. The system of claim 1, wherein the curved base has a depth substantially equal to a thickness of the ultrasonic probe such that the ultrasonic probe carrier is rotatable around the tube without interference from adjacent tubes.

9. The system of claim 1, further comprising:
a wave guide attached to the curved base, the wave guide directing ultrasonic signals from the ultrasonic probe in at least one of: a direction generally perpendicular to a longitudinal axis of the tube and a direction generally parallel to the longitudinal axis of the tube.

10. The system of claim 9, wherein the wave guide is positioned proximate the ultrasonic probe.

11. The system of claim 1, wherein the first and second side arms are pivotally attached to the curved base and are biased towards each other to removably secure the ultrasonic probe carrier around the portion of the circumference of the tube.

12. The system of claim 11, further comprising at least one spring to bias the first and second side arms toward each other.

13. The system of claim 1, wherein an arc of the curved base is open at an angle sufficient to accommodate tubes of different diameters.

14. The system of claim 1, wherein the ultrasonic probe carrier is adapted to be manually rotated around the circumference of the tube.

15. The system of claim 1, further comprising a motor coupled to the ultrasonic probe carrier to rotate the ultrasonic probe carrier around the circumference of the tube.

16. The system of claim 1, wherein the first and second side arms are biased towards each other by a magnetic force.

17. A system for performing nondestructive testing on a tube, comprising:
an ultrasonic probe carrier including:
a curved base, and
at least one side arm having a first end thereof attached to the curved base and a second end thereof extending outwardly from the curved base around the tube, at least a portion of the side arm being biased towards the curved base to removably secure the ultrasonic probe carrier around at least a portion of a circumference of the tube; and
an ultrasonic probe attached to the ultrasonic probe carrier, wherein the ultrasonic probe carrier and the ultrasonic probe are rotatable around the tube to scan at least one of the circumference of the tube and a weld disposed around the circumference of the tube.

18. The system of claim 17, further comprising:
an encoder disposed on the ultrasonic probe carrier, wherein the encoder provides a signal indicative of a location of the ultrasonic probe relative to the tube.

19. A system for performing nondestructive testing on a tube, comprising:
an ultrasonic probe carrier including a curved base extending at least partially around at least a portion of a circumference of the tube; and
an ultrasonic probe attached to the ultrasonic probe carrier and disposed internal to the curved base, wherein the ultrasonic probe carrier and the ultrasonic probe are rotatable around the tube to scan at least one of the circumference of the tube and a weld disposed around the circumference of the tube.

20. The system of claim 19, further comprising:
at least one attachment device extending outwardly from the curved base around the tube to removably secure the ultrasonic probe carrier around at least a portion of the circumference of the tube.

21. A system for performing nondestructive testing on a tube, comprising:
an ultrasonic probe carrier including:
a curved base,
a first side arm having a first end thereof attached to the curved base and a second end thereof extending outwardly from the curved base on one side of the tube, and
a second side arm having a first end thereof attached to the curved base and a second end thereof extending outwardly from the curved base on an opposite side of the tube, at least a portion of the first and second side arms being biased towards each other by a biasing force disposed at hinge points of each of the first ends of the first side arm and the second side arm, to removably secure the ultrasonic probe carrier around at least a portion of a circumference of the tube; and
an ultrasonic probe attached to the ultrasonic probe carrier, wherein the ultrasonic probe carrier and the ultrasonic probe are rotatable around the tube to scan at least one of the circumference of the tube and a weld disposed around the circumference of the tube.

22. The system of claim 21, wherein the biasing force comprises a torsion spring.

23. The system of claim 21, further comprising:
wheels disposed on each of the first and second side arms, the wheels having axes of rotation disposed generally parallel to a longitudinal axis of the tube to facilitate rotation of the ultrasonic probe carrier around the tube.

24. The system of claim 23, wherein the wheels are magnetic.

25. The system of claim 23, wherein the wheels on the first and second side arms are biased towards each other to removably secure the ultrasonic probe carrier around the portion of the circumference of the tube and the first and second arms have a curved shape.

26. The system of claim 21, further comprising:
an encoder disposed on the ultrasonic probe carrier, wherein the encoder provides a signal indicative of a location of the ultrasonic probe relative to the tube.

27. The system of claim 21, wherein the curved base has a depth substantially equal to a thickness of the ultrasonic probe such that the ultrasonic probe carrier is rotatable around the tube without interference from adjacent tubes.

28. The system of claim 21, further comprising:
a wave guide attached to the curved base, the wave guide directing ultrasonic signals from the ultrasonic probe in at least one of: a direction generally perpendicular to a longitudinal axis of the tube and a direction generally parallel to the longitudinal axis of the tube.

29. The system of claim 28, wherein the wave guide is positioned proximate the ultrasonic probe.

* * * * *